(12) United States Patent
Resler

(10) Patent No.: US 6,192,892 B1
(45) Date of Patent: Feb. 27, 2001

(54) SYSTEM AND METHOD FOR APPLYING COLOR TO A NAIL

(76) Inventor: Renee Resler, 6602 N. 31$^{st}$ St., Phoenix, AZ (US) 85016

( * ) Notice: Subject to any disclaimer, the term of this patent is extended or adjusted under 35 U.S.C. 154(b) by 0 days.

(21) Appl. No.: 09/489,512

(22) Filed: Jan. 21, 2000

(51) Int. Cl.$^7$ .................................................. A45D 29/11
(52) U.S. Cl. ............................................. 132/200; 132/73
(58) Field of Search ........................... 132/200, 73, 73.5, 132/74.5

(56) References Cited

U.S. PATENT DOCUMENTS

| | | | |
|---|---|---|---|
| 3,885,578 | * | 5/1975 | Hicks ...................................... 132/73 |
| 3,995,647 | * | 12/1976 | Kopfer ................................. 132/74.5 |
| 4,249,551 | * | 2/1981 | Nordstrom ............................. 132/73 |
| 4,450,848 | * | 5/1984 | Ferrigno ................................. 132/73 |
| 4,587,983 | * | 5/1986 | Wissman et al. ....................... 132/73 |
| 4,669,491 | * | 6/1987 | Weisberg et al. ...................... 132/73 |
| 4,687,827 | | 8/1987 | Russo . |
| 4,724,177 | | 2/1988 | Russo . |
| 5,778,901 | * | 7/1998 | Abrahmian ........................ 132/74.5 |

FOREIGN PATENT DOCUMENTS

| | | | |
|---|---|---|---|
| 4335527 | * | 2/1994 | (DE) ....................................... 132/73 |
| 2415439 | * | 9/1979 | (FR) ....................................... 132/73 |
| 392982 | * | 6/1933 | (GB) ...................................... 132/73 |

* cited by examiner

Primary Examiner—Todd E. Manahan
(74) Attorney, Agent, or Firm—Parsons & Goltry; Michael W. Goltry; Robert A. Parsons

(57) ABSTRACT

A system for applying color to a nail comprises a contained solid color material, a contained liquid solvent, and an applicator for use in picking up at least part of the liquid solvent, mixing the solvent with the solid color material to form a viscous color medium, and applying the viscous color medium to a surface of a nail.

38 Claims, 1 Drawing Sheet

SYSTEM AND METHOD FOR APPLYING COLOR TO A NAIL

FIELD OF THE INVENTION

This invention relates to fingernail color application systems and methods.

BACKGROUND OF THE INVENTION

Cosmetics comprise preparations that are applied to the human body for beautifying, preserving, or altering the appearance or for cleansing, coloring, conditioning, or protecting the skin, hair, nails, lips eyes or teeth. Since the advent of cosmetic preparations, skilled artisans have devoted considerable time and resources toward improving cosmetic preparation functionality, application systems and methods and containment structures. A particular field of cosmetics that enjoys a high degree of continuing innovation is that of nail care products, specifically, nail polish. Although most of the innovation in nail polish concerns additives designed to enhance the luster, color, texture and stability of nail polishes, relatively little attention has been devoted toward improved packaging and application methods. Given this lack of attention, the need for certain new and useful improvements directed toward nail color packaging and application methods is evident.

Accordingly, it would be highly desirable to provide a new and improved system for applying color to a surface of a nail.

It is a purpose of the invention to provide a new and improved system for applying color to a surface of a nail that is easy to construct and assemble.

It is another purpose of the invention to provide a new and improved system for applying color to a surface of a nail that incorporates packaged solid color material, packaged liquid solvent and at least one applicator.

It is still another purpose of the invention to provide a new and improved system for applying color to a surface of a nail that is easy to use.

It is a further purpose of the invention to provide a new and improved system for applying color to a surface of a nail that includes a pallet housing at least one receptacle containing a solid color material, at least one receptacle containing a liquid solvent, and one or more applicators.

It is yet a further purpose of the invention to provide a new and improved system for applying color to a surface of a nail that includes a pallet supporting a plurality of receptacles each containing a solid color material, at least one receptacle containing a liquid solvent, and one or more applicators.

It is still a further purpose of the invention to provide a new and improved system for applying color to a surface of a nail that may be easily stored and transported in a purse.

It is yet still a further purpose of the invention to provide a new and improved system for applying color to a surface of a nail that has a long shelf life.

It is another purpose of the invention to increase the ease and efficiency of applying color to a surface of a nail.

It is still another purpose of the invention to provide a new and improved method of applying color to a surface of a nail.

It is yet still another purpose of the invention to provide a packaged nail color system.

SUMMARY OF THE INVENTION

The above problems and others are at least partially solved and the above purposes and others realized in a new and improved system for applying color to a surface of a nail. The system comprises a solid color material, a liquid solvent and one of either an applicator including a working end, or a plurality of applicators each having a working end. The liquid solvent and the solid color are separate and are housed in receptacles each having a removable enclosure or lid, respectively. The receptacle containing the solid color and the receptacle containing the liquid solvent may be discrete or contained, supported or otherwise defined by a pallet or supporting structure. The pallet may be constructed to also hold or otherwise contain the applicator or applicators. In this regard, the pallet may incorporate containment structure for holding or otherwise containing the applicator or applicators. This containment structure may comprise one or more receptacles, one or more jaw or clip structures, etc. In accordance with another embodiment of the invention, the receptacle containing the solid color may be one of a plurality of receptacles each containing a solid color material. The colors of the solid color material contained in the receptacles may be of varying hues or colors. The receptacles of solid color may be discrete or contained, supported or otherwise defined by the pallet.

A preferred color application method of the invention comprises the steps of providing a contained solid color material, providing a contained liquid solvent and providing an applicator having a working end. The method further includes the steps of wetting the working end with an amount of the liquid solvent and, with the working end, mixing the amount of the liquid solvent with the solid color material to form a viscous color medium and applying the viscous color medium to a surface of a nail in the form of at least one coat.

BRIEF DESCRIPTION OF THE DRAWINGS

Referring to the drawing.

DETAILED DESCRIPTION OF A PREFERRED EMBODIMENT

Figure 1:
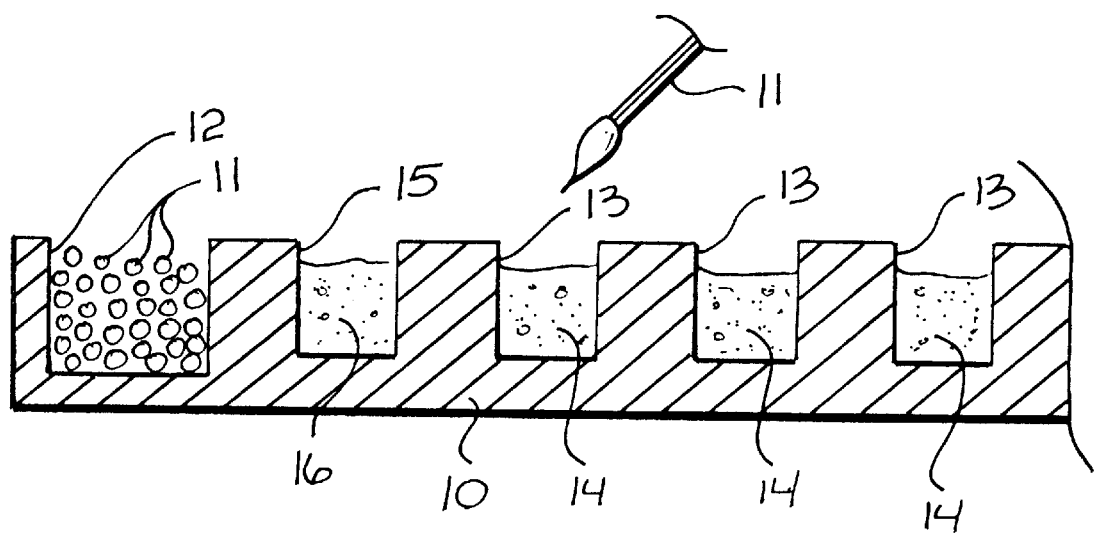
FIG. 1 is a perspective view of a nail color system in accordance with the invention.

The present invention provides, among other things, a new and improved fingernail color system and method of applying color to a surface of a fingernail. In a particular embodiment, the invention comprises a solid color material, a liquid solvent and an applicator including a working end having bristles, a pliant pad or pad-like structure, or other like structure suitable for holding and spreading a viscous liquid or polish onto a surface of a fingernail. Rather than just one applicator, the invention may incorporate a plurality of applicators and/or a plurality of disposable applicators. Each disposable applicator may, of course, be discarded after being used to apply color to a nail. The liquid solvent and the solid color material are normally housed separately in receptacles having removable enclosures or lids, respectively. The receptacles and lids may be constructed of plastic, ceramic, etc., and the lids and receptacles may incorporate structure for facilitating mutual snap, press, threaded or other desired form of engagement.

The applicator, or applicators, and receptacles containing the solid color material and the liquid solvent may be provided as a kit contained in a bag, tote, container or other container form for facilitating easy transport and storage, such as in a purse. The receptacle containing the solid color and the receptacle containing the liquid solvent may be discrete or contained, supported or otherwise defined by a pallet 10 as shown in FIG. 1 or other common support structure. In the particular embodiment shown in FIG. 1, pallet 10 is constructed to hold or otherwise contain applicators 11 and only one can be provided. In this embodiment, pallet 10 includes containment structure 12 for holding or otherwise containing the applicator or applicators 11. Containment structure 12 is shown as a receptacle and more can be employed. Jaw or clip structure, etc., may also be employed as containment structure. In another embodiment of the invention, the receptacle containing the solid color may be one of a plurality of receptacles 13 of pallet 10, each containing a solid color material 14. The colors of solid color material 14 contained in each of receptacles 13 may be of varying hues or colors. As a matter of example, pallet 10 includes a receptacle 15 of liquid solvent 16 as well, and more than one receptacle of liquid solvent can be incorporated into pallet 10 if desired.

To apply the solid color material to a surface of a fingernail, a user may open the receptacle containing the liquid solvent, open the receptacle containing solid color material, take the applicator with her hand and then briefly dip the working end of the applicator into the liquid solvent to pick up a part of the liquid solvent. With a part of the liquid solvent held by the working end of the applicator, the user may then address the solid color material with the working end and then mix the part of the liquid solvent with the solid color material to form a viscous color medium. Simply massaging the working end against the solid color material may effect this mixing. Having formed the viscous color medium, the user may then apply one or more coatings of the viscous color medium to a surface of a fingernail. With the working end holding all or part of the viscous color medium, simply brushing the working end across the surface of the fingernail may effect a coating application. This process may be repeated as necessary for effecting a plurality of nail surface coating applications to one or more fingernails. After color application, the applicator may be discarded, or the applicator may be stored for later use after rinsing the working end with the liquid solvent. It should be understood that the lids ought to be re-engaged after completing a desired number of nail surface coating applications.

Because the solid color and the liquid solvent are separate components, and not mixed together until just prior to coating application, no suspension agents or thickening agents are required, such as those required in conventional liquid nail polishes. As a result, coatings applied according to the foregoing method dry very quickly. Furthermore, by keeping the solid color and the liquid solvent separate, shelf life is greatly increased, and color hardening or drying out is eliminated.

The liquid solvent may comprise a single organic liquid solvent or a blend of organic liquid solvents. The organic solvent preferably includes one of a group including an alcohol, an ester, an ether, and a ketone. Regarding more specific embodiments, the alcohol may include one of a group including ethyl alcohol, 1-propanol, 2-propanol, methoxy ethoxy ethanol, propylene glycol, 1,4-butylene, glycol, and benzyl alcohol. The ester may include one of a group including ethyl acetate, n-propyl acetate, isopropyl acetate, n-butyl acetate, isobutyl acetate, and sec-butyl acetate. The ether may include one of a group including propylene glycol monomethyl ether, and diethylene glycol monomethyl ether. The ketone may include one of a group including acetone, dimethyl ketone, diethyl ketone, and methyl isobutyl ketone. The blend of liquid solvents may comprise a blend of any two or more of the organic solvents listed above at desired or suitable volume percentages, or any two or more of the inorganic solvents listed above at desired or suitable volume percentages. Cyclohexanone formaldehyde resin or other rosin resins may be added to the single solvent or to the blend of liquid solvents if desired.

The solid color material may comprise a solid colorant including an inorganic pigment or an organic pigment. Regarding more specific embodiments, the inorganic pigment may include one of a group including titanium dioxide, iron oxide, manganese violet, ultramarine blue, ultramarine violet, ultramarine pink, ferric ferrocyanide, chromium oxide green, chromium hydroxide green, and bismuth oxychloride. The organic pigment may include one of a group including a D and C dye, an FD and C dye, an FD and C lake, an oil soluble D and C dye, and a D and C lake. Depending on specific needs, the inorganic pigment may include a blend of any two or more of the above group of inorganic pigments at desired volume percentages. The organic pigment may also include a blend of any two or more of the above group of organic pigments at desired volume percentages. Both organic dyes and inorganic pigments may also be used in the form of RS nitrocellulos dispersion to provide color.

To help extend the solid color material and to help the viscous color medium spread easily and adhere, the solid color material may be provided with a filler. The filler be incorporated at a suitable or desired volume percent, and may include one of a group including talc, kaolin, mica magnesium carbonate, Fuller's earth, wollastonite, gypsum, dolomite, alumina silicates, silica, quartz, calcium carbonate, and bentone. The filler may also include a blend of any two or more of the foregoing group of fillers at desired volume percentages. The solid color material may also be provided with a plasticizer at a suitable or desired volume percent to help the solid colorant incorporate into the final solid color material. The plasticizer may include one of a group including dibutyl phthalate, dioctyl phthalate, di-2-ethyl hexyl phthalate, diisononyl phthalate, a C7–11 alkyl phthalate mixture, di-2-ethylhexyl adipate, diisononyl adipate, N-ethyl o/p toluenesulfonamide, mineral oil, octyl palmitate, and trioctyl trimellitate. The plasticizer may also include a blend of any two or more of the foregoing group of plasticizers at desired volume percentages. To aid dispersion of the solid colorant, the solid color material may further include a modifier at a suitable or desired volume percent. The modifier may include one of a group including lithium stearate, magnesium stearate, zinc stearate, and lanolin.

In another embodiment, the solid color material may also be provided with a preservative. The preservative helps preserve the solid color material and may be provided at a suitable or desired volume percent. The preservative may include one of a group including a methyl paraben, a propyl paraben, and an imidazolidinyl urea. The preservative may also include a blend of any two or more of the foregoing group of preservatives at desired volume percentages. A film former may also be incorporated into the solid color material at a suitable or desired volume percent. The film former may include one of a group including a methacrylate polymer, a methacrylate copolymer, nitrocellulose, a toluenesulfonamide-formaldehyde polymer, a toluenesulfonamide-epoxy resin, polyvinyl acetate, polyvinyl butyral, nylon, a cellulose ester, polycarbonate, a terminated polymethacrylate, polyurethane, and a polyester of a diol of terephthalate. The film former may also include a blend of any two or more of the foregoing group of film formers at desired volume percentages.

To enhance the ability of the solid color material to mix with the liquid solvent, the liquid solvent may be provided with a plasticizer at a suitable or desired volume percent. This plasticizer may include one or more of a group including dibutyl phthalate, dioctyl phthalate, di-2 -ethyl hexyl phthalate, diisononyl phthalate, a C7–11 alkyl phthalate mixture, di-2-ethylhexyl adipate, diisononyl adipate, N-ethyl o/p toluenesulfonamide, mineral oil, octyl palmitate, and trioctyl trimellitate. The plasticizer may also include a blend of any two or more of the foregoing group of plasticizers at desired volume percentages. A film former may also be incorporated into the liquid solvent at a suitable or desired volume percent. This film former may include one of a group including a methacrylate polymer, a methacrylate copolymer, nitrocellulose, a toluenesulfonamide-formaldehyde polymer, a toluenesulfonamide-epoxy resin, polyvinyl acetate, polyvinyl butyral, nylon, a cellulose ester, polycarbonate, a terminated polymethacrylate, polyurethane, and a polyester of a diol of terephthalate. The film former may also include a blend of any two or more of the foregoing group of film formers at desired volume percentages. In yet another embodiment, the liquid solvent may further include a hydroxy methacrylate monomer. This hydroxy methacrylate monomer may include one a group including hydroxyethyl methacrylate, hydroxypropyl methacrylate, hydroxybutyl methacrylate, polyethylene glycol methacrylate, polyethylene glycol dimethacrylate, and polypropylene glycol methacrylate. The hydroxy methacrylate monomer may also include a blend of any two or more of the foregoing group of hydroxy methacrylate monomers at desired volume percentages.

The invention has been described above with reference to one or more preferred embodiments. However, those skilled in the art will recognize that changes and modifications may be made in the described embodiments without departing from the nature and scope of the invention. Various changes and modifications to one or more of the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A nail color system comprising:
   receptacles each containing a solid nail color material, wherein the color of the solid nail color material of each receptacle is different;
   a container of liquid solvent; and
   an applicator having a working end for use in picking up at least part of the liquid solvent from the container, mixing the part with the solid color material by massaging the working end against the solid color material of a given one of the receptacles to form a viscous color medium, and in applying the viscous color medium to a surface of a nail.

2. The system of claim 1, wherein the liquid solvent includes a hydroxy methacrylate monomer.

3. The system of claim 2, wherein the hydroxy methacrylate monomer includes one or more of a group including hydroxyethyl methacrylate, hydroxypropyl methacrylate, hydroxybutyl methacrylate, polyethylene glycol methacrylate, polyethylene glycol dimethacrylate, and polypropylene glycol methacrylate.

4. The system of claim 1, wherein the solid nail color material of each one of the receptacles includes one of an inorganic pigment and an organic pigment.

5. The system of claim 4, wherein the inorganic pigment includes at least one of a group including titanium dioxide, iron oxide, manganese violet, ultramarine blue, ultramarine violet, ultramarine pink, ferric ferrocyanide, chromium oxide green, chromium hydroxide green, and bismuth oxychloride.

6. The system of claim 4, wherein the organic pigment includes at least one of a group including D and C dye, FD and C dye, FD and C lake, oil soluble D and C dye, and D and C lakes.

7. The system of claim 1, wherein the solid nail color material of each one of the receptacles includes a filler.

8. The system of claim 7, wherein the filler includes at least one a group comprising talc, kaolin, mica magnesium carbonate, Fuller's earth, wollastonite, gypsum, dolomite, alumina silicates, silica, quartz, calcium carbonate, and bentone.

9. The system of claim 1, wherein the solid nail color material of each one of the receptacles includes a plasticizer.

10. The system of claim 9, wherein the plasticizer includes at least one of a group including dibutyl phthalate, dioctyl phthalate, di-2-ethyl hexyl phthalate, diisononyl phthalate, a C7–11 alkyl phthalate mixture, di-2-ethylhexyl adipate, diisononyl adipate, N-ethyl o/p toluenesulfonamide, mineral oil, octyl palmitate, and trioctyl trimellitate.

11. The system of claim 1, wherein the solid nail color material of each one of the receptacles includes a modifier.

12. The system of claim 11, wherein the modifier includes at least one of a group including lithium stearate, magnesium stearate, zinc stearate, and lanolin.

13. The system of claim 12, wherein the preservative includes at least one of a group including a methyl paraben, a propyl paraben, and an imidazolidinyl urea.

14. The system of claim 1, wherein the solid nail color material of each one of the receptacles includes a preservative.

15. The system of claim 1, wherein the solid nail color material of each one of the receptacles includes a film former.

16. The system of claim 15, wherein the film former includes at least one of a group including a methacrylate polymer, a methacrylate copolymer, nitrocellulose, a toluenesulfonamide-formaldehyde polymer, a toluenesulfonamide-epoxy resin, polyvinyl acetate, polyvinyl butyral, nylon, a cellulose ester, polycarbonate, a terminated polymethacrylate, polyurethane, and a polyester of a diol of terephthalate.

17. The system of claim 1, wherein the liquid solvent includes an organic solvent.

18. The system of claim 17, wherein the organic solvent includes at least one selected from a group including an alcohol, an ester, an ether, and a ketone.

19. The system of claim 18, wherein the alcohol includes one or more of a group including ethyl alcohol, 1-propanol, 2-propanol, methoxy ethoxy ethanol, propylene glycol, 1,4-butylene, glycol, and benzyl alcohol.

20. The system of claim 18, wherein the ester includes one or more of a group including ethyl acetate, n-propyl acetate, isopropyl acetate, n-butyl acetate, isobutyl acetate, and sec-butyl acetate.

21. The system of claim 18, wherein the ether includes one or more of a group including propylene glycol monomethyl ether, and diethylene glycol monomethyl ether.

22. The system of claim 18, wherein the ketone includes one or more of a group including acetone, dimethyl ketone, diethyl ketone, and methyl isobutyl ketone.

23. The system of claim 1, wherein the liquid solvent includes a plasticizer.

24. The system of claim 23, wherein the plasticizer includes at least one of a group including dibutyl phthalate, dioctyl phthalate, di-2-ethyl hexyl phthalate, diisononyl phthalate, a C7–11 alkyl phthalate mixture, di-2-ethylhexyl adipate, diisononyl adipate, N-ethyl o/p toluenesulfonamide, mineral oil, octyl palmitate, and trioctyl trimellitate.

25. The system of claim 1, wherein the liquid solvent includes a film former.

26. The system of claim 25, wherein the film former includes at least one of a group including a methacrylate polymer, a methacrylate copolymer, nitrocellulose, a toluenesulfonamide-formaldehyde polymer, a toluenesulfonamide-epoxy resin, polyvinyl acetate, polyvinyl butyral, nylon, a cellulose ester, polycarbonate, a terminated polymethacrylate, polyurethane, and a polyester of a diol of terephthalate.

27. A method of applying color to a surface of a nail comprising the steps of:

providing a first receptacle containing a solid nail color material;

providing a second receptacle containing a liquid solvent;

providing an applicator having a working end;

wetting the working end with an amount of the liquid solvent contained by the second receptacle;

with the working end, mixing the amount of the liquid solvent with the solid color material by massaging the working end against the solid nail color material to form a viscous color medium; and with the working end, applying the viscous color medium to a surface of a nail in the form of at least one coat.

28. A nail color system comprising:

a first receptacle containing a solid nail color material;

a second receptacle containing a liquid solvent; and an applicator having a working end for use in picking up at least part of the liquid solvent from the container, mixing the part with the solid color material by massaging the working end against the solid color material to form a viscous color medium, and in applying the viscous color medium to a surface of a nail.

29. The system of claim 28, wherein the solid nail color material includes one of an inorganic pigment and an organic pigment.

30. The system of claim 28, wherein the solid nail color material includes a filler.

31. The system of claim 28, wherein the solid nail color material includes a plasticizer.

32. The system of claim 28, wherein the solid nail color material includes a modifier.

33. The system of claim 28, wherein the solid nail color material includes a preservative.

34. The system of claim 28, wherein the solid nail color material includes a film former.

35. The system of claim 28, wherein the liquid solvent includes an organic solvent.

36. The system of claim 28, wherein the liquid solvent includes a plasticizer.

37. The system of claim 28, wherein the liquid solvent includes a film former.

38. The system of claim 28, wherein the liquid solvent includes a hydroxy methacrylate monomer.

* * * * *